(12) United States Patent
Knochel et al.

(10) Patent No.: US 7,387,751 B2
(45) Date of Patent: Jun. 17, 2008

(54) METHOD OF PREPARING ORGANOMAGNESIUM COMPOUNDS

(75) Inventors: Paul Knochel, Munich (DE); Arkady Krasovskiy, Munich (DE)

(73) Assignee: Ludwig-Maximilians-Universitat Munchen, Munich (DE)

( * ) Notice: Subject to any disclaimer, the term of this patent is extended or adjusted under 35 U.S.C. 154(b) by 0 days.

(21) Appl. No.: 11/787,974

(22) Filed: Apr. 18, 2007

(65) Prior Publication Data

US 2007/0194468 A1   Aug. 23, 2007

Related U.S. Application Data

(62) Division of application No. 11/097,707, filed on Apr. 1, 2005.

(30) Foreign Application Priority Data

Apr. 2, 2004   (EP)   ................................ 04008081

(51) Int. Cl.
*C07F 3/04* (2006.01)
(52) U.S. Cl. ................................. 260/665 G
(58) Field of Classification Search ............. 260/665 G
See application file for complete search history.

(56) References Cited

OTHER PUBLICATIONS

Dumouchel et al., Synthesis and reactivity of lithium tri(quinolinyl)magnesates, Tetrahedron, 59 (2003), 8629-8640.*

* cited by examiner

*Primary Examiner*—Yvonne Eyler
*Assistant Examiner*—Chukwuma O Nwaonicha
(74) *Attorney, Agent, or Firm*—Jenkins, Wilson, Taylor & Hunt, P.A.

(57) ABSTRACT

The present invention is directed to a reagent for use in the preparation of organomagnesium compounds as well as to a method of preparing such organomagnesium compounds. The present invention furthermore provides a method of preparing functionalized or unfunctionalized organic compounds as well as the use of the reagents of the present invention in the preparation of organometallic compounds and their reaction with electrophiles. Finally, the present invention is directed to the use of lithium salts—LiY in the preparation of organometallic compounds and their reactions with electrophiles and to an organometallic compound which is obtainable by the disclosed method.

18 Claims, 3 Drawing Sheets

METHOD OF PREPARING ORGANOMAGNESIUM COMPOUNDS

CROSS REFERENCE TO RELATED APPLICATIONS

This application is a divisional of pending U.S. patent application Ser. No. 11/097,707, filed Apr. 1, 2005, which claimed priority to European Patent Application EP 04008081.4, filed Apr. 2, 2004. The disclosures of each of these applications is incorporated herein by reference in its entirety.

TECHNICAL FIELD

The present invention is directed to a reagent for use in the preparation of organomagnesium compounds as well as to a method of preparing such organomagnesium compounds. The present invention furthermore provides a method of preparing organic compounds. It further provides the use of the reagents of the present invention in the preparation of organometallic compounds and their reaction with electrophiles. Finally, the present invention is directed to the use of lithium salts—LiY in the preparation of organometallic compounds and their reactions with electrophiles and to an organometallic compound which is obtainable by the disclosed method.

BACKGROUND OF THE INVENTION

Polyfunctionalized organometallics are important intermediates in modern organic synthesis.[1]

One of the best preparative methods of these reagents is the halogen-metal exchange reaction. Whereas the Br/Li-exchange is a fast reaction which occurs at low temperature, the corresponding Br/Mg-exchange is considerably slower, which is a severe synthetic limitation for several reasons:
 (i) the exchange requires higher reaction temperature and therefore is not compatible with many functional groups,
 (ii) the slow Br/Mg-exchange especially on electron-rich aromatic bromides is in competition with the elimination of HBr from the alkyl bromide also produced during the reaction (usually isopropyl bromide) and therefore, results in low yields. A catalysis of the Br/Mg-exchange would be a highly desirable process.

Recently, the co-inventors have shown that highly functionalized aryl- and heteroaryl-magnesium halides can be readily prepared by using an iodine-magnesium exchange reaction.[2] As exchange reagent i-PrMgX (X=Cl, Br) proves to be most convenient. In some cases, this exchange reaction could be extended to some aryl and heteroaryl bromides when a powerful electron-withdrawing and (or) a chelating group was present to coordinate i-PrMgX and make, the Br—Mg exchange "intramolecular".[3]

Basically, the I/Mg-exchange reaction is an excellent method for preparing functionalized aryl and heteroaryl compounds. It has as main drawback the need of using sometimes unstable, often expensive or commercially not available organic iodides. The alternative of using aryl bromides as substrates for the Br/Mg-exchange is known, but was strongly limited to only highly reactive aryl bromides (bearing several electron-withdrawing groups) due to the low rate of the exchange reaction using either i-PrMgCl or i-Pr$_2$Mg.

Therefore, it is a problem underlying the present invention to provide an improved method of preparing organomagnesium compounds. It is a further problem underlying the present invention to provide an organomagnesium compound, which has a higher reactivity with an electrophile (E+).

These problems are solved by the subject-matter of the independent claims. Preferred embodiments are set forth in the dependent claims.

SUMMARY OF THE INVENTION

The inventors found that by using the mixed organometallic $R^1(MgX)_n \cdot LiY$, a fast exchange reaction occurs leading to the desired Grignard reagents in high yields under mild conditions and allowing the preparation of many functionalized Grignard compounds which were previously only available via Br/Mg-exchange reactions in mediocre yields. The method of the present invention considerably facilitates in particular the preparation of aryl-, heteroaryl-, alkenyl-, alkinyl or alkyl-magnesium compounds and finds broad applications in university as well as in industrial laboratories for large scale use. Basically, the method of the present invention corresponds to the following reaction scheme:

According to a first aspect, the invention is directed to a reagent for use in the preparation of organomagnesium compounds, the reagent having the general formula:

$R^1(MgX)_n \cdot LiY$ wherein:

n is 1 or 2;

$R^1$ is a substituted or unsubstituted $C_4$-$C_{24}$ aryl or $C_3$-$C_{24}$ heteroaryl, containing one or more heteroatoms as B, O, N, S, Se, P, F, Cl, Br, I, Si; linear or branched, substituted or unsubstituted $C_1$-$C_{20}$ alkyl, $C_2$-$C_{20}$ alkenyl or $C_2$-$C_{20}$ alkinyl; or substituted or unsubstituted $C_3$-$C_{20}$ cycloalkyl; or a derivative thereof;

X and Y are independently or both Cl, Br or I, preferably Cl; HalO$_n$ (where n=3, 4); carboxylate of formula RCO$_2$; alkoxide or phenoxide of formula RO; dialkoxide of formula LiO—R—O; disilazide of formula (R$_3$Si)$_2$N; thiolate of formula SR; RP(O)O$_2$; or SCOR; where R is defined as $R^1$ above; $C_1$-$C_{20}$ linear or branched, substituted or unsubstituted alkyl or $C_3$-$C_{20}$ cycloalkyl amine of formula RNH; dialkyl/arylamine of formula R$_2$N (where R is defined as above or R$_2$N represents a heterocyclic alkylamine); phosphine of formula PR$_2$ (where R is defined as above or PR$_2$ represents a heterocyclic phosphine); O$_n$SR (where n=2 or 3 and R is defined as above); or NO$_n$ (where n=2 or 3); or X=$R^1$ as defined above; and a derivative thereof.

It is noted that X and $R^1$ usually will be the same substituent in the case of X=$R^1$, however may also be different in the scope of the definition indicated for $R^1$.

It is explicitly noted that the present invention also comprises compounds of formula XMg—$R^1$—MgX.LiY (i.e., where n=2). Furthermore, whenever "R$_2$" is indicated in this application (for example in R$_2$N or PR$_2$), both R's may be the same or may be different according to the definition indicated above.

Additionally, it surprisingly turned out that the exchange rate using $R^1(MgX)_n \cdot LiY$ can be further enhanced, if X=$R^1$. This reagent is achieved by addition of polyethers or polyamines that lead to the formation of new reagent $(R^1)_2Mg \cdot LiY$.

Thus, in a preferred embodiment, the reagent is $(R^1)_2Mg \cdot LiY$.

The mechanism involved in this unexpected finding may be explained as follows:

It is noted that this system usually requires to use at least one solvent as outlined below and at least one additive (see also below). For example THF might be used as a solvent alone or in combination with other solvents, and a crown-ether as outlined above might be used as additive, which is directly involved in the formation of the reagent is $(R^1)_2Mg.LiY$.

There might be exceptions to that general rule in that some solvents may be used also as additive or vice versa. For example, it is possible to prepare $(R^1)_2Mg.LiY$ in pure dioxane as outlined below.

Dioxane has several advantageous properties, it is a, for example, cheap, non-toxic, industrial, not easily flammable, high boiling, not very hydroscopic solvent that is easy to handle and to make dry—thus a practically ideal solvent and additive. And, it serves as a suitable additive and solvent in the above reactions.

As an example for the above reaction, the reagent is made in situ by treating simply a solution of i-PrMgCl.LiCl with a crown-ether such as 15-crown-5 (which gives the best result; see entry 4 of Table 3) or more generally with another polyether or polyamine, see Table 3. Remarkably, and as mentioned above, the cheapest way to achieve the rate enhancement is to use the addition of dioxane (10% vol) which lead to 100% of conversion (4-bromoanisole to 4-methoxy-phenylmagnesium chloride) after 24 h reaction time. For comparison the performance of the same reaction with i-PrMgCl.LiCl in THF gives only 31-39% conversion after the same time. It is also important to notice that the addition of 15-crown-5 or dioxane to i-PrMgCl without LiCl does not lead to any rate enhancement.

Thus, the addition of 1,4-dioxane (or related polyethers like oligo- or polyethyleneglycol ethers or polyamines) will further enhance exchange reactions such as the Br/Mg-exchange and allow to convert e.g. bromides into the corresponding Grignard reagents under conditions which before led to uncomplete reaction. Further explanations for this may be found in chapter "Examples".

According to one embodiment, the reagent comprises $R_1(MgX)_n$ and LiY in a molar ratio of between 0.05-6.0.

According to a preferred embodiment, Y is Cl in $R^1(MgX)_n.LiY$ or LiY. In an even more preferred embodiment, $R^1(MgX)_n.LiY$ is i-PrMgCl.LiCl or sec-BuMgCl.LiCl. The preferred molar ratios between i-PrMgCl or sec-BuMgCl and LiCl are 0.05 to 6.0.

According to a further preferred embodiment, Y in $R^1(MgX)_n.LiY$ or LiY is tert-butylate or sec-butylate. Other lithium salts like lithium perchlorate, lithium acetylacetonate, lithium bromide, lithium iodide and lithium tetrafluoroborate are also included in this invention, however, are less preferred embodiments.

According to a second aspect, the present invention provides a method of preparing organomagnesium compounds, comprising the following steps:

a) providing a compound having the general formula:

$R^2A$;

wherein $R^2$ is defined as $R^1$ or is a substituted or unsubstituted metallocene such as ferrocene; or a derivative thereof.

A is H, Cl, Br, I, preferably Br, or a group of the general formula:

$S(O)_n—R^3$ wherein n=0, 1 or 2 or a group of the general formula:

$P(O)R^3_2$ wherein R³ independently is defined as R¹ above. It is noted that R³ in this context may be the same or different.

or P(O)R³₂ represents a heterocyclic phosphinoxide;

b) providing a reagent according to the formula R¹(MgX)ₙ.LiY as defined above;

c) reacting the compounds provided in step a) and b) under suitable conditions;

thereby obtaining the respective organomagnesium compound.

The organomagnesium compound obtained in c) can additionally be isolated.

It is noted that, if R² is an aryl or heteroaryl compound, it may be substituted by one or more groups FG, wherein FG is preferably selected from F, Cl, Br, CN, CO₂R, OR, OH, NR₂, NHR, NH₂, PR₂, P(O)R₂, CONR₂, CONHR, SR, SH, CF₃, NO₂, C=NR, R (wherein R is defined as R¹ above). Preferred examples of R²A are bromonapthalene, bromophenanthrene, bromoanisole, bromothiophene, bromothiazole, bromopyridine, 1-bromo-3-fluorobenzene, 3-bromobenzothiophene, 1,2-dibromobenzene, 1,2,4 tribrombenzene and derivatives thereof as well as the further compounds disclosed hereinafter.

Principally it is possible to use all kinds of functional groups FG that are, for example, cited in the following references, but are not limited thereto:

a) Handbook of Grignard reagents; edited by Gary S. Silverman and Philip E. Rakita (Chemical industries; v. 64).

b) Grignard reagents New Developments; edited by Herman G. Richey, Jr., 2000, John Wiley & Sons Ltd.

c) Methoden der Organischen Chemie, Houben-Weyl, Band XIII/2a, Metallorganische Verbindungen Be, Mg, Ca, Sr, Ba, Zn, Cd. 1973.

d) The chemistry of the metal-carbon bond, vol 4. edited by Frank R. Hartley. 1987, John Wiley & Sons.

According to a further embodiment, the reagent of the general formula R¹(MgX)ₙ.LiY is provided by reacting R¹X, Mg and LiY or by reacting R¹(MgX)ₙ and LiY, or by reacting R¹Li and MgXY. It is noted that some components for use in this reaction are commercially available and thus, are not required to be synthesized de novo (for example, i-PrMgCl for R¹MgX is commercially available from Aldrich or Strem CAS [1068-55-9]).

According to an embodiment, the reagent provided in step b) is used in a molar amount of 0.4-6.0 mole per mole of the compound provided in step a). In general, the reagent of the present invention having the general formula R¹(MgX)ₙ.LiY can be added up to 6,0 mole of the reagent to 1 mole of compound provided in a) (general formula R²A). The lower limit of 0.4 mole per mole R²A means that the effects of the present invention, i.e. the spectacular rate increase in the conversion reaction:

may not be achieved, if values lower than this limit will be used.

It is noted that in the above formula, n may be different in R¹(MgX)ₙ.LiY and R²(MgX)ₙ.LiY.

The above reaction is carried out in a suitable solvent. Preferably, the solvent, in which R¹(MgX)ₙ.LiY is dissolved is an inert aprotic solvent, for example tetrahydrofuran, diethyl ether, 2-methyltetrahydrofuran, dibutyl ether, tert-butylmethyl ether, dimethoxyethane, dioxane, triethylamine, pyridine, ethyldiisopropylamine, dichlormethane, 1,2-dichlorethane, dimethylsulfide, dibutylsulfide, benzene, toluene, xylene, pentane, hexane or heptane, or combinations thereof and/or solvents usually used for performing of Grignard reactions that are indicated in the literature cited above.

As outlined above, adding one or more additives to the solvent may yield an improved reagent (R¹)₂Mg.LiY. This additive may be selected from polyethers or polyamines, in particular crown ethers, dioxanes, oligo- or polyethylenegylcol ethers, derivatives of urea, amides of formula RCONR₂ (where R is defined as in claim 1, radicals may be same or different), most preferably 1,4-dioxane or 15-crown-5 or combinations thereof. Further examples of additives which might be used in the present invention are listed in Table 3, below.

According to a further embodiment, the above solution of R¹(MgX)ₙ.LiY is 0.05 to 3.0 M, preferably 1.0-2.5 M. As a general rule, the higher the concentration of the solution is, the better the overall reaction will work. However, generally, more than 3 M solutions of R¹(MgX)ₙ.LiY will no more be soluble and thus will not function in this invention.

The use of R¹(MgX)ₙ.LiY as a powder (without solvents or with coordinated solvents) is also possible and especially convenient for storage.

According to a further aspect, the invention provides a method for preparing functionalized or unfunctionalized organic compounds, comprising steps a)-c) as defined above, and d) reacting the obtained organomagnesium compound with an organic or inorganic electrophile (E+) or (E).

The reaction follows the reaction scheme:

Examples of electrophiles which are commonly used for the reaction with Grignard reagents are cited in references a)-d) mentioned above, but not limited thereto.

Specific examples for the electrophile are RCHO, RCOX, XₙPR₃₋ₙ(n=1, 2, 3), XₙP(O)R₃₋ₙ (n=1, 2, 3), RX, RCO₂R, RCN, RₙSi—X₄₋ₙ(n=0, 1, 2, 3), RₙSnX₄₋ₙ(n=0, 1, 2, 3) or RSSOₙR (n=0, 1, 2), RNO₂, RNO, RN=NSO₂R, RC=NR, B(OR)₃, wherein X is a halogen or S(O)ₙR group, wherein n=0, 1 or 2, and R is generally defined as R¹ above.

Again, it is noted that, where two or three R's are contained in one formula, they can be the same or different from each other.

However, the invention is not restricted to these examples and improved reactions of the Grignard reagents complexed with LiY with various electrophiles are observed for all types of electrophiles.

The methods mentioned above are performed at a temperature in a range between −78° C. to 80° C., preferably at room temperature. The upper limit of the temperature range generally is the boiling temperature of the respective solvent used.

According to a further aspect the invention is directed to the use of the reagent R¹(MgX)ₙ·LiY in the preparation of organometallic compounds and their reaction with electrophiles.

A further aspect of the invention is directed to the use of LiY in the preparation of organometallic compounds and their reaction with electrophiles, wherein Y is defined as above. It is noted that in particular LiCl turned out to dramatically increase the conversion rates in the above exchange methods. For comparison, see enclosed Table 2.

According to a final aspect, the invention provides an organometallic compound, which is obtainable by the method in accordance with the second aspect as defined above. It is noted that the complexed product of this reaction, i.e. a product of general formula R²(MgX)ₙ·LiY, has a much higher reactivity with electrophile (E+) or (E) than the prior art reagents and also its solubility in the respective suitable solvents (see above) is superior.

Thus, by the methods of the present invention it is possible to achieve conversion rates of up to 100% compared to only mediocre yields of the prior art methods.

The present invention will be further described with reference to the following figures and examples; however, it is to be understood that the present invention is not limited to such figures and examples.

DETAILED DESCRIPTION OF THE INVENTION

The present invention will now be described more fully hereinafter with reference to the accompanying figures. The following embodiments are rather provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications and other references mentioned herein are incorporated by reference in their entirety.

As used herein, the terms "alkyl", "alkenyl" and "alkinyl" refer to linear and branched, substituted and unsubstitued $C_1$-$C_{20}$ compounds. Preferred ranges for these compounds are $C_1$-$C_{10}$, preferably $C_1$-$C_5$ (lower alkyl) and $C_2$-$C_{10}$ and preferably $C_2$-$C_5$, respectively, for alkenyl and alkinyl. The term "cycloalkyl" generally refers to linear and branched, substituted and unsubstituted $C_3$-$C_{20}$. Here, preferred ranges are $C_3$-$C_{15}$, more preferably $C_3$-$C_8$.

The term "aryl" as used herein refers to substituted or unsubstituted $C_4$-$C_{24}$ aryl. By "heteroaryl", a substituted or unsubstituted $C_3$-$C_{24}$ heteroaryl, containing one or more heteroatoms as B, O, N, S, Se, P, is meant. Preferred ranges for both are $C_4$-$C_{15}$, more preferably $C_4$-$C_{10}$.

The inventors now found that it is possible to catalyze exchange reactions, for example the Br/Mg-exchange reaction by using the complex R¹(MgX)ₙ·LiY, for example i-PrMgCl·LiCl. As an example, 1-bromo-3-fluorobenzene (1a) undergoes only a slow incomplete exchange reaction with i-Pr₂Mg (1.1 equiv, rt, 3h) leading after the reaction with benzaldehyde to the corresponding alcohol 2a in 50% isolated yield.[3a] On the other hand, the reaction with i-PrMgCl·LiCl under the same conditions provides the intermediate magnesium reagent 3a with 95% yield as judged by GC-analysis using tetradecane as internal standard. After a reaction with benzaldehyde, the alcohol 2a is obtained in 85% isolated yield (Scheme 1).

Various fluoro- and chloro-substituted aryl bromides are readily converted into the corresponding magnesium reagents at room temperature using i-PrMgCl·LiCl. The conversion is completed without 0.5-3 h which is in strong contrast with the previous procedure involving i-PrMgCl or i-Pr₂Mg (Scheme 2).

Scheme 2. Reaction Times of the Preparation of Arylmagnesium Reagents with i-PrMgCl.LiCl.

Similarly, this catalysis can be applied to heterocyclic systems like 2,6-dibromopyridine (1b). This dibromide requires also the use of i-Pr₂Mg[3a] or i-PrMgCl[3f] for performing the Br/Mg-exchange reaction. Under these conditions, the reaction with benzaldehyde provides the desired alcohol 2ba in only 42% yield.[3f] We have observed again the superiority of i-PrMgCl.LiCl as exchange reagent and have observed a conversion of 92% after reaction time of 1 h at 25° C. whereas the use of i-Pr₂Mg requires a reaction time of 4 h. Using the new reagent i-PrMgCl.LiCl, the desired reaction product (2ba) is obtained in 89% isolated yield (Scheme 1). Also good results were obtained in the reactions of formed Grignard reagent (3b) from 2,6-dibromopyridine (1b) with other electrophiles (Table 1, entries 1-3). The Br/Mg-exchange in the case of 3,5-dibromopyridine can be performed in 15 min at −10° C. and the reaction with allyl bromide provides allylated pyridine 2ca in excellent yield (Table 1, entry 4). Less activated 3-bromopyridine can be also easily converted to the corresponding Grignard reagent 3v within 5 min. at room temperature and led after the reaction with allyl bromide to the 3-allylpyridine 2va with almost quantitative yield. Other heterocyclic systems such as 2-bromothiophene, 3-bromothiophene, 3-bromobenzothiophene and 2-bromothiazole react easily with i-PrMgCl.LiCl at room temperature and after reaction with various electrophiles provide corresponding products 2ra-2ua with good to excellent yields (Table 1, entries 29-32). It should be especially noted that our approach opened way for the synthesis of different aldehydes through the reaction of Grignard reagent 3r with different electrophiles because thiazole group can be easily converted to the aldehyde function.

This behavior is general and the use i-PrMgCl.LiCl allows a faster Br/Mg-exchange compared to i-PrMgCl or i-Pr₂Mg. Also, it increases dramatically the conversion leading to the desired organomagnesium reagent without the need of an excess of reagent (usually 1.1 or 1.05 equiv of i-PrMgCl.LiCl is used). Furthermore, the reactivity of the resulting magnesium reagent seems also to be improved and leads to higher yields in trapping reactions with electrophiles. Sterically hindered Grignard reagents bearing a substituent in ortho position like 31 are obtained within 12 h reaction time at rt furnishing after the addition of benzaldehyde the desired alcohol 21a in 90% yield (Table 1, entry 21). The more electron-rich the aromatic ring is, so slower the exchange reaction using i-PrMgCl. 2-Methoxy-1-bromobenzene (1h) is however converted to the desired magnesium reagent 3h in more than 90% yield after a reaction time of 24 h at rt. After its reaction with PhSSPh the thioether 2ha is obtained in 90% yield (entry 12). A range of different electrophiles reacts with these Grignard reagents after a transmetalation step with CuCN.2LiCl[4] allowing the performance of allylations and acylations (entry 14).

Figure 3:
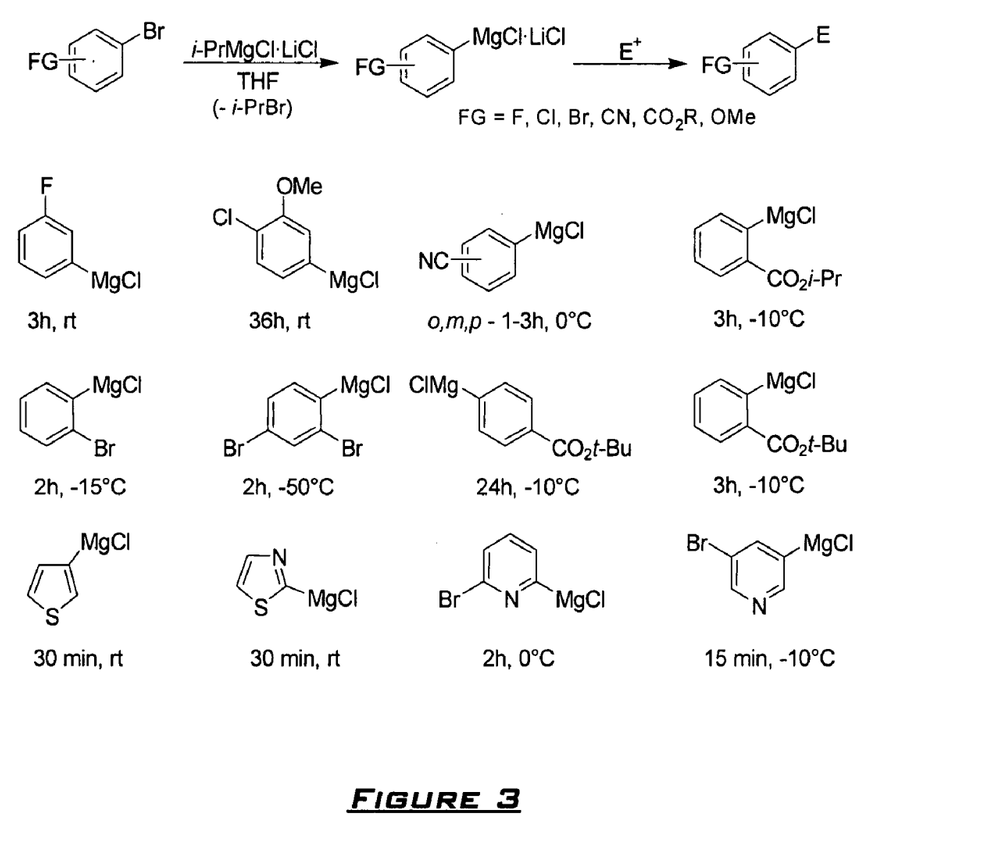
FIG. 3 is a reaction scheme for the preparation of Grignard reagents prepared in over 90% by the Br/Mg exchange using i-PrMgCl·LiCl (the reaction conditions are given below each formula).

Highly substituted chloro and methoxy aryl bromides can readily be converted into the desired Grignard reagents 3i, j. After the reaction with ClPPh₂ and oxidative work-up, the phosphine oxides 2ia, ja are obtained in good yields (entry 15, 16). This type of compound is of interest in relation with P-ligands for asymmetric catalysis.[5] Also functions like a cyano group are tolerated. Thus, the reaction of 4-bromobenzonitrile in THF at −7° C. leads to the desired arylmagnesium reagent (3d) in only 50% conversion using i-PrMgCl whereas over 90% is observed with i-PrMgCl-.LiCl (Scheme 3). The addition of benzaldehyde provides the alcohol 2da in 81% yield whereas allylation of arylmagnesium reagent (3d) with allyl bromide leads to the corresponding 4-allylbenzonitrile in 92% yield (entry 5,6 of Table 1). See FIG. 3 for additional information.

The Grignard reagents 3e, f is formed within 3 h at 0° C. and showed good yields after the reactions with various electrophiles (entries 5-10). Usually unreactive compounds like bromonaphthalene and bromophenanthrene derivatives are readily converted into the corresponding Grignard reagents 3m, n (entries 22-25) that easily react both with benzaldehyde (entries 22, 24) and with allyl bromide in good yields (entry 23). After catalytic transmetallation with CuCN.2LiCl (0.2 equiv.) and reaction with ethyl 4-iodobutyrate 4h at −10° C., the desired cross-coupling product 2nb is obtained in 81% yield (entry 25). As noticed above, various dichloro-substituted Grignard reagents like 3o and 3p can be readily prepared and react with aromatic and aliphatic aldehydes furnishing the corresponding alcohols 2oa, 2pa in 83 and 92% yield (entries 26, 27). Also ester function can be tolerated in ortho-position, thus magnesium reagent 3q was prepared within 12 h at −45° C. and reaction with allyl bromide leads to the formation of corresponding allylated ester 2qa in 82% yield.

Remarkably, in the case of 1,2-dibromobenzenes only a mono exchange reaction occurs providing the desired Grignard reagent (3k) (−15° C., 1.5 h) in almost quantitative yield as indicated by GC-analysis of reaction aliquots. The reaction of 2-bromophenylmagnesium chloride (3k) with 3-iodo-2-cyclohexen-1-one produces the expected enone (2kc) in 86% yield. The Grignard reagent 3k also showed good activity towards different electrophiles (entries 17-20). Various variations of these reactions and several important new magnesium reagents are reported in entries 21-33 of Table 1.

Since the stereoselective preparation of stereochemically well defined E- or Z-alkenylmagnesium compounds is not possible by the direct insertion of magnesium into the E- or Z-alkenyl halides, the iodine-magnesium exchange reaction may be unique way of preparing stereochemically pure E- or Z-alkenylmagnesium derivatives.[6] Recently, we have shown that the iodine-magnesium exchange reactions in case of alkenyl iodides demand the presence of electron withdrawing group in α- or,β-position to facilitate the exchange reaction.[7] This led us to investigate the stereoselective preparation of alkenylmagnesium reagents via I/Mg-exchange from non activated iodo- alkenes. Thus, the reaction of (E)-1-bromohexene exchange reaction occurs providing the (E)-1-hexenymagnesium chloride (4a) (−25° C., 10 h) in almost quantitative yield (GC-analysis of reaction aliquots). The reaction of Grignard reagent 4a with t-BuCHO led to the formation of corresponding alcohols 5a with excellent yield. This remarkably low temperature will allow the presence of numerous functional groups. Also, we observed a fast exchange reaction with good coversion (GC) in the case of a chiral cyclic alkenyl iodide. Subsequent reaction of magnesium reagent 4b with allyl bromide proceeds in good yield that opened the access to the different α-substituted chiral allylic alcohols (Scheme 3).

Scheme 3.

-continued

5a, 83%

It is also possible to do Br/Mg-exchange in vinylic systems. Thus 1,2-dibromocyclopenten easily react with i-PrMgCl.LiCl at room temperature to produce stable Grignard reagent 4c that after reaction with cyclohexyl aldehyde gave corresponding alcohol 5b in good yield.

Scheme 4.

Reagent 4c is completely stable at room temperature for weeks, but addition of catalitical amounts of Cu(I) or Cu(II) leads to the formation of cyclopentine that in the presence of additional equivalent of magnesium or lithium compounds reacts with the formation of new Grignard spieces 4d,e. Addition of benzaldehyde gave corresponding alcoholes in good yields.

Figure 1:
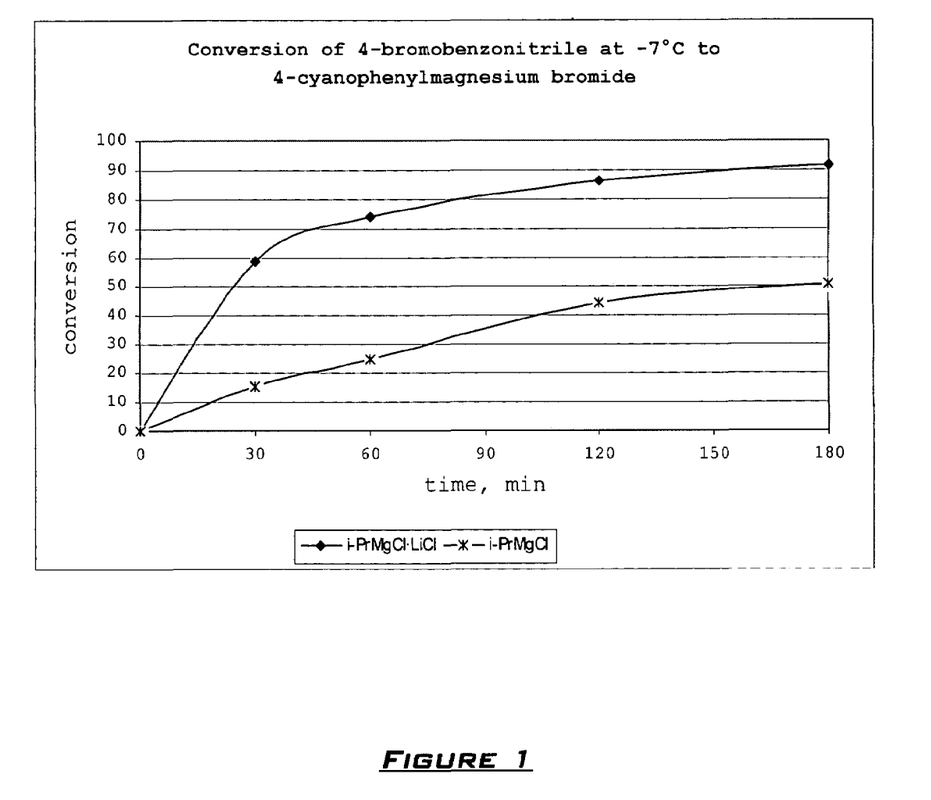
FIG. 1 is a graph showing the conversion of 4-bromobenzonitrile at −7° C. to 4-cyanophenylmagnesium bromide.
Figure 2:
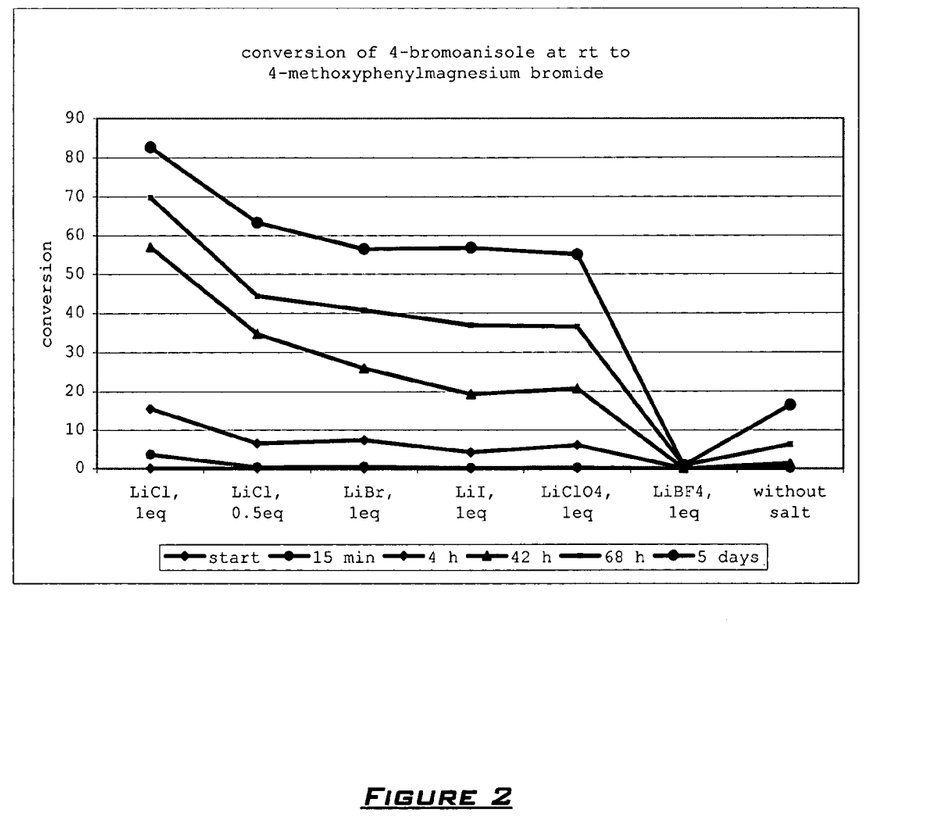
FIG. 2 is a graph showing the conversion of 4-bromoanisole at room temperature to 4-methoxyphenylmagnesium bromide.

Other lithium salts like lithium perchlorate, lithium acetylacetonate, lithium bromide, lithium iodide and lithium tetrafluoroborate were also tested, but gave less efficient catalysis (FIG. 2).

Although the mechanism of the catalysis is not elucidated, the inventors assume that the role of lithium chloride is to activate i-PrMgCl by increasing the nucleophilic character of the isopropyl group by forming a magnesiate species of type 6 leading to the ate-intermediate of type 7 and finally to the organomagnesium species PhMgCl.LiCl (8).

The complexation of the arylmagnesium species with LiCl as indicated for 8 (Scheme 6) may also be responsible for the enhanced reactivity of these magnesium organometallics.[4]

As an example, the inventors found a simple procedure for catalyzing the Br/Mg-exchange reaction of aryl and heteroaryl bromides with the complex i-PrMgCl.LiCl. It allows to prepare a range of new polyfunctional organomagnesium compounds starting from cheap aryl and heteroaryl bromides containing the most important functionalities for organic synthesis.

EXAMPLE 1

Preparation of the Reagent i-PrMgCl.LiCl

Magnesium turnings (110 mmole) were placed in an Ar-flushed flask with anhydrous LiCl (100 mmole) and 50 ml of THF were added. The solution of i-PrCl (100 mmole) in 50 ml of THF was added slowly and the mixture was stirred at rt and the Grignard formation starts within a few minutes. The reaction mixture was stirred after the completing of exothermical reaction for additional 12 h at rt. Slightly dark solution of i-PrMgCl.LiCl was transferred to a new flask under Ar and removed in this way from excess of Mg.

Typical procedure. Preparation of phenyl-(4-cyanophenyl)methanol 2da. A dry and argon flushed 10 mL flask, equipped with a magnetic stirrer and a septum, was charged with 4-bromobenzonitrile (182 mg, 1 mmole). Dry THF (1 mL) was added, the reaction mixture was cooled to −7° C. and i-PrMgCl.LiCl (1 mL, 1.1 M in THF, 1.1 mmole) was then added dropwise. The Br/Mg-exchange was complete after 3 h (checked by GC analysis of reaction aliquots, conversion more than 90%) and benzaldehyde (116.6 mg, 1.1 mmole) was added. The reaction mixture was stirred for 0.5 h at −7° C. and was then quenched with sat. NH$_4$Cl solution (2 mL). The aqueous phase was extracted with ether (3×4 mL) and the organic fractions were washed with brine (5 mL), dried (Na$_2$SO$_4$) and concentrated in vacuo. The crude residue was purified by flash chromatography (dichloromethane) yielding the benzylic alcohol (2da) as a colourless oil (169.5 mg, 81%). $^1$H-NMR (CDCl$_3$, 200 MHz): δ=7.91-7.85 (m, 2 H); 7.65-7.46 (m, 3 H); 7.38-7.30 (m, 4 H); 5.86 (s, 1 H); 2.42 (s, 1 H, OH).

Preparation of 3-allyl-5-bromopyridine 2ca. A dry and argon flushed 10 mL flask, equipped with a magnetic stirrer and a septum, was charged with i-PrMgCl.LiCl (1 mL, 1.05 M in THF, 1.05 mmole), the reaction mixture was cooled to −15° C. and 3,5-dibromopyridine (236.9 mg, 1 mmole) was then added at one portion. The temperature than increased till −10° C. and the Br/Mg-exchange was complete after 15 min (checked by GC analysis of reaction aliquots, conversion more than 98%), allyl bromide (140.6 mg, 1 mmole) was added. The reaction mixture was stirred for 1 h at −10° C. and was then quenched with sat. NH$_4$Cl solution (2 mL). The aqueous phase was extracted with ether (3×4 mL), dried (Na$_2$SO$_4$) and concentrated in vacuo. The crude residue was purified by flash chromatography (dichloromethane) yielding the 3-allyl-5-bromopyridine (2ca) as a colourless oil (184.2 mg, 93%). $^1$H-NMR (CDCl$_3$, 200 MHz): δ=8.48 (d, J=2.2 Hz, 1 H); 8.32 (d, J=1.6 Hz, 1 H); 7.61 (dd, J=2.2 Hz, J=1.6 Hz, 1 H); 5.89-5.68 (m, 1 H); 5.08-5.01 (m, 1 H); 3.32 (brd, J=6.8 Hz, 1 H).

Preparation of (2-bromophenyl)(phenyl)methanone 2ka. A dry and argon flushed 10 mL flask, equipped with a magnetic stirrer and a septum, was charged with i-PrMgCl.LiCl (1 mL, 1.05 M in THF, 1.05 mmole), the reaction mixture was cooled to −15° C. and 1,2-dibromobenzene (235.9 mg, 1 mmole) was then added dropwise. The Br/Mg-exchange was complete after 1.5 h (checked by GC analysis of reaction aliquots, conversion more than 98%) and solution of CuCN.2LiCl (0.1 mL, 1.0 M in THF, 0.1 mmole) was added. After stirring for 10 min at −15° C. benzoyl chloride (140.6 mg, 1 mmole) was added. The reaction mixture was stirred for 1 h at −15° C. and was then quenched with sat. NH$_4$Cl solution (2 mL) and also 5 drops of concentrated NH$_3$ was added. The aqueous phase was extracted with ether (3×4 mL) and the organic fractions were washed with brine (5 mL), dried (Na$_2$SO$_4$) and concentrated in vacuo. The crude residue was purified by flash chromatography (dichloromethane) yielding the ketone (2ka) as a white cristals (219.3 mg, 84%). $^1$H-NMR (CDCl$_3$, 200 MHz): δ=7.86-7.78 (m, 2 H); 7.68-7.56 (m, 2 H); 7.52-7.30 (m, 5 H).

TABLE 1

Products of Type 2 Obtained by the Reaction of the Organomagnesium Reagents 3 Obtained by an Exchange of Aryl and Heteroaryl Bromides with i-PrMgCl•LiCl with Various Electrophiles

| Entry | Grignard reagent[a] | Electrophile | Product of type 2 | | Yield (%)[b] |
|---|---|---|---|---|---|
| 1 |  3b | allyl bromide |  | 2bb | 80[c] |
| 2 |  3b | PhCOCl |  | 2bc | 77[c] |
| 3 |  3b | t-BuCHO |  | 2bd | 94 |
| 4 |  3c | allyl bromide |  | 2ca | 93 |

TABLE 1-continued

Products of Type 2 Obtained by the Reaction of the Organomagnesium Reagents 3 Obtained by an Exchange of Aryl and Heteroaryl Bromides with i-PrMgCl•LiCl with Various Electrophiles

| Entry | Grignard reagent[a] | Electrophile | Product of type 2 | | Yield (%)[b] |
|---|---|---|---|---|---|
| 5 |  3d | PhCHO |  | 2da | 81 |
| 6 |  3d | allyl bromide |  | 2db | 92 |
| 7 |  3e | allyl bromide |  | 2ea | 93[c] |
| 8 |  3e | PhCOCl |  | 2eb | 87[c] |
| 9 |  3f | allyl bromide |  | 2fa | 95 |
| 10 |  3f | PhCOCl |  | 2fb | 88[c] |

TABLE 1-continued

Products of Type 2 Obtained by the Reaction of the Organomagnesium
Reagents 3 Obtained by an Exchange of Aryl and Heteroaryl Bromides with
i-PrMgCl•LiCl with Various Electrophiles

| Entry | Grignard reagent[a] | Electrophile | Product of type 2 | | Yield (%)[b] |
|---|---|---|---|---|---|
| 11 | 3g (4-MeO-C6H4-MgX) | PhCHO | 4-MeO-C6H4-CH(OH)-Ph | 2ga | 70 |
| 12 | 3h (2-MeO-C6H4-MgX) | PhSSPh | 2-MeO-C6H4-S-Ph | 2ha | 90 |
| 13 | 3h | PhCHO | 2-MeO-C6H4-CH(OH)-Ph | 2hb | 84 |
| 14 | 3h | PhCOCl | 2-MeO-C6H4-CO-Ph | 2hc | 81[c] |
| 15 | 3i (3-MeO-4-Cl-C6H3-MgX) | ClPPh2 | 3-MeO-4-Cl-C6H3-P(O)Ph2 | 2ia | 85[d] |
| 16 | 3j (3-MeO-C6H4-MgX) | ClPPh2 | 3-MeO-C6H4-P(O)Ph2 | 2ja | 80[d] |
| 17 | 3k (2-Br-C6H4-MgX) | PhCOCl | 2-Br-C6H4-CO-Ph | 2ka | 84[c] |
| 18 | 3k | allyl bromide | 2-Br-C6H4-CH2-CH=CH2 | 2kb | 92 |

TABLE 1-continued

Products of Type 2 Obtained by the Reaction of the Organomagnesium
Reagents 3 Obtained by an Exchange of Aryl and Heteroaryl Bromides with
i-PrMgCl•LiCl with Various Electrophiles

| Entry | Grignard reagent[a] | Electrophile | Product of type 2 | | Yield (%)[b] |
|---|---|---|---|---|---|
| 19 |  3k |  |  | 2kc | 86[c] |
| 20 |  3k | PhCHO |  | 2kd | 81 |
| 21 |  3l | PhCHO |  | 2la | 90 |
| 22 |  3m | PhCHO |  | 2ma | 91 |
| 23 |  3m | allyl bromide |  | 2mb | 93 |
| 24 |  3n | PhCHO |  | 2na | 94 |

TABLE 1-continued

Products of Type 2 Obtained by the Reaction of the Organomagnesium Reagents 3 Obtained by an Exchange of Aryl and Heteroaryl Bromides with i-PrMgCl•LiCl with Various Electrophiles

| Entry | Grignard reagent[a] | Electrophile | Product of type 2 | | Yield (%)[b] |
|---|---|---|---|---|---|
| 25 | 3n | I(CH$_2$)$_3$CO$_2$Et | | 2nb | 81[c] |
| 26 | 3o | PhCHO | | 2oa | 83 |
| 27 | 3p | t-BuCHO | | 2pa | 92 |
| 28 | 3q | allyl bromide | | 2qa | 82 |
| 29 | 3r | PhCHO | | 2ra | 87 |
| 30 | 3s | PhCHO | | 2sa | 81 |
| 31 | 3t | PhCHO | | 2ta | 90 |

TABLE 1-continued

Products of Type 2 Obtained by the Reaction of the Organomagnesium
Reagents 3 Obtained by an Exchange of Aryl and Heteroaryl Bromides with
i-PrMgCl•LiCl with Various Electrophiles

| Entry | Grignard reagent[a] | Electrophile | Product of type 2 | Yield (%)[b] |
|---|---|---|---|---|
| 32 |  3u | PhCOCl |  | 2ua 85[c] |
| 33 |  3v | allyl bromide |  | 2va 96 |

[a]X = Cl•LiCl;
[b]Isolated yield of analytically pure product;
[c]The Grignard reagent was transmetalated with CuCN•2LiCl before reaction with an electrophile;
[d]The reaction mixture was worked up oxidatively with aq. H$_2$O$_2$.

TABLE 2

| Entry[a] | Additive | Equiv. | Conversion. [%] |
|---|---|---|---|
| 1 | — | — | 18 |
| 2 | LiBF$_4$ | 1.0 | 5 |
| 3 | LiBr | 1.0 | 40 |
| 4 | LiI | 1.0 | 38 |
| 5 | LiClO$_4$ | 1.0 | 38 |
| 6 | LiCl | 1.0 | 70 |
| 7 | LiCl | 0.25 | 22 |
| 8 | LiCl | 0.5 | 43 |
| 9 | LiCl | 1.5 | 73 |
| 10 | LiCl | 2.0 | 74 |
| 11 | LiCl | 1.0 | 84[b] |

[a]The conversion of the reaction was determined by gas chromatographical analysis of reaction aliquots; precision ±2%.
[a]The concentration of i-PrMgCl•LiCl was 2.22M.

EXAMPLE 2

Improved Behavior of Reagents (R$^1$)$_2$Mg.LiY

The reaction of aryl bromide 1 with i-PrMgCl.LiCl leads only to mixture, whereas with i-PrMgCl.LiCl in THF with the addition of 15-crown-5 leads to 91% conversion to the corresponding Grignard reagent 2.

TABLE 3

Effect of the Addition of Additives on the Formation of
4-Methoxyphenylmagnesium Chloride at 25° C. After 24 Hour
Reaction Time (1 M solution in THF).

| Entry | Additive | Equiv. | Conversion. [%][a] |
|---|---|---|---|
| 1 | - | - | 7 |
| 2 | LiCl | 1.0 | 31 (iPrMgCl) 32 (secBuMgCl) |
| 3 | LiCl | 1.0 | 39[b] |
| 4 | LiCl + 15-C-5 | 1.0/1.0 | A: 100 B: 100 (6 h) |
| 5 | LiCl + 15-C-5 | 1.0/0.5 | A: 88 |
| 6 | LiCl + 15-C-5 | 1.0/0.1 | A: 54 |
| 7 | LiCl + 18-C-6 | 1.0/1.0 | A: 59 B: 77 |
| 8 | LiCl + 12-C-4 | 1.0/1.0 | A: 30 B: 28 |
| 9 | LiCl + PEG250 | 1.0/10% vol | A: 64 B: 55 |
| 10 | LiCl + MeO(CH$_2$CH$_2$O)$_3$OMe | 1.0/10% vol | A: 47 B: 58 |
| 11 | LiCl + MeO(CH$_2$CH$_2$O)$_4$OMe | 1.0/10% vol | A: 52 B: 60 |

TABLE 3-continued

Effect of the Addition of Additives on the Formation of
4-Methoxyphenylmagnesium Chloride at 25° C. After 24 Hour
Reaction Time (1 M solution in THF).

| Entry | Additive | Equiv. | Conversion. [%][a] |
|---|---|---|---|
| 12 | LiCl + dioxane | 1.0/10% vol | A: 91 (88)[c] |
|    |                |             | B: 100 |
| 13 | LiCl + dioxane | 1.0/5% vol | B: 70 |
| 14 | LiCl + dioxane | 1.0/20% vol | B: 100 |
| 15 | 15-C-5 | 1.0 | A: 8 |
| 16 | dioxane | 10% vol | A: 8 |
| 17 | LiCl + DMPU | 1.0/10% vol | B: 60 |
| 18 | LiCl + MTBE | 1.0/10% vol | B: 27 |
| 19 | LiCl + TMEDA | 1.0/10% vol | A: 68 |
|    |              |             | B: 77 |
| 20 | LiCl + DME | 1.0/10% vol | B: 70 |
| 21 | LiCl + TMU | 1.0/10% vol | B: 48 |
| 22 | LiCl + NMM | 1.0/10% vol | B: 20 |
| 23 | LiCl + DABCO | 1.0/1.0 | B: 11 |
| 24 | LiCl + DBU | 1.0/10% vol | B: 49 |

[a]The conversion of the reaction was determined by gas chromatographical analysis; precision ±2%.
[b]The concentration of i-PrMgCl·LiCl was 2.22 M.
[c]In brackets conversion for the reaction with filtrated reagent.

ABBREVIATIONS

15-C-5: 15-crown-5
PEG 250: Polyethyleneglycol, mean molecular weight 250 g/mol
DMPU: tetrahydro-1,3-dimethyl-2(1H)-pyrimidinone,
MTBE: 2-methoxy-2-methyl-propane,
TMU: N,N,N',N'-tetramethyl-urea,
NMM: N-methylmorpholine Method A: 4-bromoanisole was added to the pre-stirred mixture of secBuMgCl.LiCl and additive at 25° C.
Method B: Additive was added to the pre-stirred mixture of secBuMgCl.LiCl and 4-bromoanisole

REFERENCES

[1] A. Boudier, L. O. Bromm, M. Lotz, P. Knochel, *Angew. Chem.*, 2000, 112, 4584; *Angew. Chem. Int. Ed.* 2000, 39, 4414.
[2] a) P. Knochel, W. Dohle, N. Gommermann, F. F. Kneisel, F. Kopp, T. Korn, I. Sapountzis, V. A. Vu, *Angew. Chem.* 2003, 115, 4438, *Angew. Chem. Int. Ed.* 2003, 42, 4302; b) L. Boymond, M. Rottländer, G. Cahiez, P. Knochel, *Angew. Chem.* 1998, 110, 1801; *Angew. Chem. Int. Ed.* 1998, 37,1701;
[3] a) M. Abarbri, F. Dehmel, P. Knochel, *Tetrahedron Lett.* 1999, 40, 7449; for the synthesis of arylmagnesium species starting from aryl bromides using lithium organomagnesiates for performing the Br/Mg-exchange reaction: b) K. Kitagawa, A Inoue, H. Shinokubo, K. Oshima, *Angew. Chem.* 2000 112, 2594; *Angew. Chem. Int. Ed.* 2000 39, 2481; c) A Inoue, K. Kitagawa, H. Shinokubo, K. Oshima, *J. Org. Chem.* 2001, 66, 4333; d) A. Inoue, K. Kitagawa, H. Shinokubo, K. Oshima, *Tetrahedron* 2000, 56, 9601; e) F. Trécourt, G. Breton, V. Bonnet, F. Mongin, F. Marsais,; G. Queguiner, *Tetrahedron Lett.* 1999, 40, 4339. f) F. Trécourt, G. Breton, V. Bonnet, F. Mongin, Marsais, G. Quéguiner, *Tetrahedron* 2000, 56, 1349.
[4] a) P. Knochel, M. C. P. Yeh, S. C. Berk, J. Talbert, *J. Org. Chem.* 1988, 53, 2390; b) P. Knochel, N. Millot, A. L. Rodriguez, C. E. Tucker, *Org. React.* 2001, 58, 417.
[5] P. Torsten, P. Thomas, G. Guido, S. Wolfgram. *Eur. Pat. Appl.* (2002).
[6] The direct insertion of magnesium into alkenyl halides is not stereoselective. For example, the reaction of (Z)-1-bromooctene with magnesium in THF produces a 15:85 E:Z mixture of 1-octenylmagnesium bromide. The same behaviour is observed for the insertion of zinc dust into alkenyl iodides. In both cases, a radical mechanism operates. T. N. Majid and P. Knochel, *Tetrahedron. Lett.*, 1990, 31, 4413.
[7] I. Sapountzis, W. Dohle, P. Knochel, *Chem. Commun.* 2001, 2068.

What is claimed is:

1. A method for preparing an organomagnesium compound, the method comprising:
   (a) providing a reagent having the general formula:

$R^1(MgX)_n \cdot LiY$ wherein:
   n is 1 or 2;
   $R^1$ is a substituted or unsubstituted $C_4$-$C_{24}$ aryl or $C_3$-$C_{24}$ heteroaryl, containing one or more heteroatoms selected from the group consisting of B, O, N, S, Se, P, F, Cl, Br, I, and Si; linear or branched, substituted or unsubstituted $C_1$-$C_{20}$ alkyl, $C_2$-$C_{20}$ alkenyl or $C_2$-$C_{20}$ alkinyl; or substituted or unsubstituted $C_3$-$C_{20}$ cycloalkyl; and
   X and Y are independently or both Cl, Br or I, $HalO_m$, where m=3 or 4; carboxylate of formula $RCO_2$; alkoxide or phenoxide of formula RO; dialkoxide of formula LiO—R—O; disilazide of formula $(R_3Si)_2N$; thiolate of formula SR, $RP(O)O_2$, or SCOR, where R is $R^1$ as defined above; linear or branched substituted or unsubstituted $C_1$-$C_{20}$ alkyl or $C_3$-$C_{20}$ cycloalkyl amine of formula RNH; dialkylamine or diarylamine of formula $R_2N$, where R is defined as above or $R_2N$ represents a heterocyclic alkylamine; phosphine of formula $PR_2$, where R is defined as above or $PR_2$ represents a heterocyclic phosphine; $O_pSR$, where p=2 or 3 and R is defined as above; or $NO_q$, where q=2 or 3; or $X=R^1$ as defined above;
   (b) providing a compound having the general formula $R^2A$, wherein:
   $R^2$ is a substituted or unsubstituted metallocene; or $R^2$ is $R^1$, wherein $R^1$ is as defined above, provided that $R^2$ and $R^1$ are not identical; and
   A is H, Cl, Br, I; a group of the general formula $S(O)_r$-$R^3$, wherein r=0, 1, or 2; a group of the general formula $P(O)R^3_2$, where $P(O)R^3_2$ is a heterocyclic phosphinoxide or each $R^3$ is independently $R^1$ as defined above; and
   (c) reacting the compounds provided in steps (a) and (b), whereby an organomagnesium compound is prepared having the general formula $R^2(MgX)_n \cdot LiY$.

2. The method of claim 1, wherein the reagent is provided by reacting:
   (i) $R^1X$, Mg, and LiY;
   (ii) $R^1(MgX)_n$ and LiY; or
   (iii) $R^1Li$ and MgXY.

3. The method of claim 1, wherein the reagent is present in reacting step (c) in a molar amount of 0.4-6.0 per mole of the compound.

4. The method of claim 1, wherein the reagent is present in reacting step (c) as a solution in a suitable solvent.

5. The method of claim 4, wherein the solvent is selected from tetrahydrofuran, 2-methyltetrahydrofuran, dibutyl ether, diethyl ether, tert-butylmethyl ether, dimethoxyethane, dioxanes, triethylamine, pyridine, ethyldiisopropylamine, dichlormethane, 1,2-dichlorethane, dimethylsulfide, dibutylsulfide, benzene, toluene, xylene, pentane, hexane, heptane, or combinations thereof.

6. The method of claim 5, wherein the dioxane is 1,4-dioxane.

7. The method of claim 4, wherein the solution further comprises one or more additives selected from the group consisting of polyethers, polyamines, dioxanes, oligoethyleneglycol ethers, polyethyleneglycol ethers, N,N,N'N'-tetramethyl-urea (TMU), amides of formula $RCONR_2$, wherein each R is independently defined as in claim 1; and combinations thereof.

8. The method of claim 7, wherein the one or more additives comprise one or more crown ethers.

9. The method of claim 7, wherein the one or more additives is selected from among 1,4-dioxane and 15-crown-5.

10. The method of claim 4, wherein the solution is 0.05 M to 3.0 M $R^1$ $(MgX)_n \cdot LiY$.

11. The method of claim 10, wherein the solution is 1.0 M to 2.5 M.

12. The method of claim 1, wherein the metallocene is ferrocene.

13. The method of claim 1, wherein X, Y, or both X and Y are Cl.

14. The method of claim 1, wherein A is Br.

15. The method of claim 1, wherein the method further comprises reacting the organomagnesium compound obtained from step (c) with an organic or inorganic electrophile (E+) or (E) to produce a functionalized or unfunctionalized organomagnesium compound.

16. The method of claim 15, wherein the electrophile is selected from the group consisting of RCHO; RCOX; $X_sPR_{3-s}$, where s=1, 2, or 3; $X_tP(O)R_{3-t}$, where t=1, 2, or 3; RX, $RCO_2R$, RCN, $R_uSi-X_{4-u}$, where u=0, 1, 2, or 3, $R_vSnX_{4-v}$, where c=0, 1, 2, or 3; $RSSO_wR$, where w=0, 1, or 2); $RNO_2$; RNO; RN=$NSO_2R$; RC=NR; and $B(OR)_3$, wherein X is a halogen or $S(O)_yR$ group, where y=0, 1 or 2, and R is $R^1$ as defined in claim 1.

17. The method of one of claims 1 and 15, wherein the reacting is performed at a temperature in a range between −78° C. and 80° C.

18. The method of claim 17, wherein the reacting is performed at room temperature.

* * * * *